United States Patent [19]

Amplatz et al.

[11] Patent Number: 5,620,438
[45] Date of Patent: Apr. 15, 1997

[54] METHOD AND APPARATUS FOR TREATING VASCULAR TISSUE FOLLOWING ANGIOPLASTY TO MINIMIZE RESTENOSIS

[75] Inventors: Curtis A. Amplatz, St. Paul, Minn.; Christopher H. Porter, Woodinville, Wash.; Mark A. Rydell, Golden Valley, Minn.

[73] Assignee: AngioMedics II Incorporated, Minneapolis, Minn.

[21] Appl. No.: 425,858

[22] Filed: Apr. 20, 1995

[51] Int. Cl.⁶ .................................................. A61N 5/06
[52] U.S. Cl. .................................... 606/10; 606/3; 606/7; 606/15; 606/17
[58] Field of Search ................... 606/2, 3, 7, 10–18, 606/194

[56] References Cited

U.S. PATENT DOCUMENTS

| | | | |
|---|---|---|---|
| Re. 34,544 | 2/1994 | Spears | 604/20 |
| 4,266,548 | 5/1981 | Davi | 606/14 |
| 4,336,809 | 6/1982 | Clark | 128/665 |
| 4,470,407 | 9/1984 | Hussein | 128/6 |
| 4,512,762 | 4/1985 | Spears | 604/21 |
| 4,648,892 | 3/1987 | Kittrell et al. | 606/7 |
| 4,791,926 | 12/1988 | Fry | 606/7 |
| 4,799,479 | 1/1989 | Spears | 606/194 |
| 4,862,886 | 9/1989 | Clarke et al. | 128/303.1 |
| 4,985,028 | 1/1991 | Ismer et al. | 606/15 |
| 5,053,033 | 10/1991 | Clarke | 606/3 |
| 5,207,669 | 5/1993 | Baker et al. | 606/7 |
| 5,207,672 | 5/1993 | Roth et al. | 606/7 |
| 5,441,497 | 8/1995 | Narcuso, Jr. | 606/7 |

*Primary Examiner*—David M. Shay
*Attorney, Agent, or Firm*—Haugen and Nikolai, P.A.

[57] ABSTRACT

A surgical instrument for treating a blood vessel wall following percutaneous transluminal coronary angioplasty (PTCA) includes an optical system for transmitting radiant energy, preferably UV light energy, from a laser source to the distal end portion a PTCA catheter and causing the radiant energy to exit the catheter in a relatively narrow radial band. A microprocessor-controlled stepping motor is used to longitudinally reposition the band along the length of the balloon of the PTCA catheter to thereby expose endothelial tissue spanned by the balloon to radiation for the purpose of inhibiting smooth muscle proliferation reducing incidences of restenosis.

15 Claims, 1 Drawing Sheet

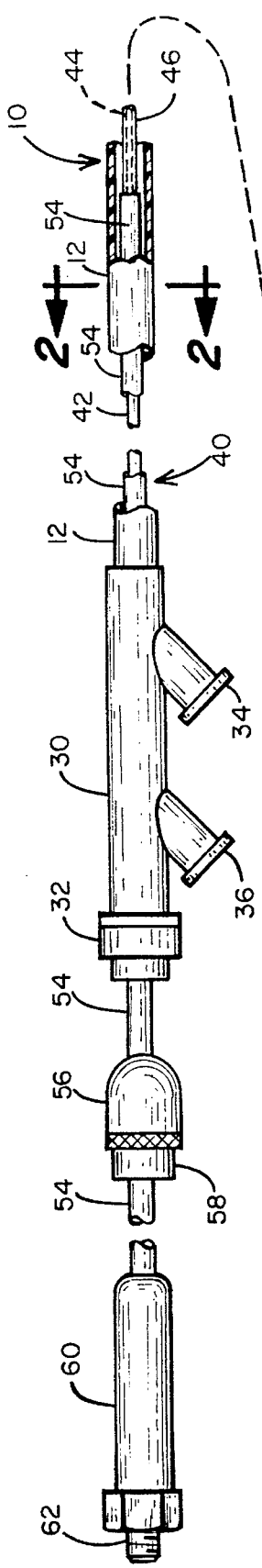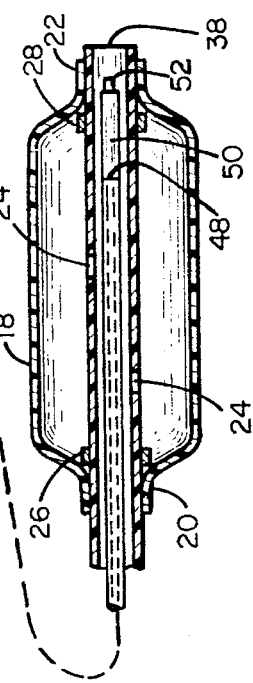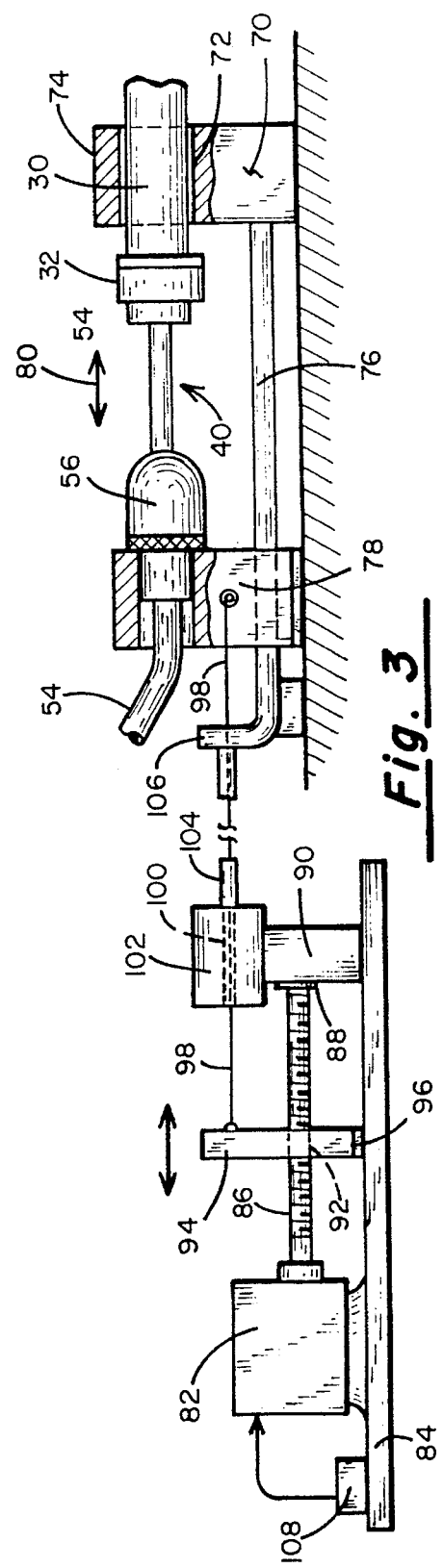
Fig. 1
Fig. 2
Fig. 3

METHOD AND APPARATUS FOR TREATING VASCULAR TISSUE FOLLOWING ANGIOPLASTY TO MINIMIZE RESTENOSIS

BACKGROUND OF THE INVENTION

I. Field of the Invention

This invention relates generally to surgical instruments for improving the outcome of percutaneous transluminal coronary angioplasty procedures, and more particularly to a catheter having a means for irradiating a treatment site with radiant energy, e.g., UV light, to reduce the incidences of restenosis.

II. Discussion of the Prior Art

Percutaneous transluminal coronary angioplasty (PTCA) has become a recognized method of reducing the occlusion of blood vessels due to coronary artery disease. The procedure involves routing a catheter having an inflatable balloon at the distal end thereof through the vascular system until the balloon is positioned at the site of the stenotic lesion to be treated. The balloon is then inflated to compress the atherosclerotic plaque into the wall of the coronary artery, thus increasing the size of the opening and enhancing blood flow through the affected artery. Approximately 400,000 angioplasty procedures are performed annually in the United States to open blocked coronary arteries. However, this successful procedure is overshadowed by the occurrence of restenosis, a re-narrowing of the artery. Studies have shown that 30–40 percent of angioplasty patients experience restenosis within six months of the angioplasty procedure. When restenosis occurs, patients may be treated with cardiovascular medications, additional angioplasty procedures or bypass surgery. Carrying out the angioplasty procedure results in damage to the endothelium and it is found that the body's natural response to such damage is a proliferation of smooth muscle cells, oftentimes resulting in restenosis.

In U.S. Pat. No. 5,053,033 to Richard H. Clarke, a technique is described for reducing incidences of restenosis following angioplasty. The patent describes a procedure in which the blood vessel walls at the angioplasty site are irradiated with UV light during the course of the angioplasty procedure and that the effect of such irradiation is to reduce proliferation of smooth muscle cells at the site of the damage. In accordance with the teachings of the Clarke patent, the UV radiation is delivered by means of an optical fiber incorporated into a percutaneous catheter. The UV radiation is sent down the optical fiber from a suitable laser or even a source of non-coherent UV light. It is theorized that ultraviolet light in the 240 nm to 280 nm range, when delivered to the DNA of smooth muscle cells effects cellular replication, thereby inhibiting proliferation.

In U.S. Pat. No. Reissue 34,544 to Spears, there is described a system for performing angioplasty which also uses light energy typically in the infrared range. In accordance with that patent, the subject is first injected with a hematoporphyrin which is selectively taken up into the atheromatous plaque. Subsequently, light in the IR range is made to impinge on the stenotic lesion, resulting in lysis of the plaque. A balloon catheter equipped with a flexible optical fiber is used to deliver the light to the source. When the balloon is inflated, it displaces the otherwise opaque blood allowing transmission of the IR energy through the balloon to the plaque being irradiated.

While research, to date, has been limited, medical scientists have been exploring the use of gamma radiation in treating damage to blood vessel walls resulting from angioplasty and/or atherectomy procedures.

Neither the Spears Reissue U.S. Pat. No. 34,544 nor the Clarke U.S. Pat. No. 5,053,033 teaches an apparatus for providing a uniform exposure of the intimal and endothelial layers at the site of the treated stenosis to radiation, such as UV light, over the entire area of the compressed lesion, nor precise control over the exposure time. Moreover, the liquid filled, hollow glass tube 24 at the distal end of the catheter 12 in the Spears patent would be relatively rigid and thus likely to cause damage to a vessel wall as the catheter carrying this structure is advanced through the vascular system. In the Clarke patent, the balloon 42 is deflated during the attempted exposure of the treated tissue to UV light. Hence, blood will surround the optical lens at the distal end of the catheter and effectively reduce the transmission of UV light to the tissue to be irradiated, thereby necessitating longer exposure times.

Thus, it can be seen from the foregoing a need exists for an improved instrument for exposing the area of compressed lesion to radiant energy in a controlled manner following balloon angioplasty so as to reduce the tendency toward smooth muscle growth and restenosis. It is a principal purpose of the present invention to satisfy this need.

SUMMARY OF THE INVENTION

In accordance with the present invention, there is provided an apparatus for treating the wall of a blood vessel following a balloon angioplasty procedure to reduce a subsequent occurrence of restenosis. The apparatus comprises a conventional angioplasty catheter of the type having a tubular catheter body with a proximal end, a distal end portion and first and second lumens extending through the tubular body. An inflatable balloon of a predetermined length dimension is disposed proximate the distal end portion of the catheter body and the interior of the balloon is in fluid communication with the first lumen. Both the distal end portion of the tubular catheter body and the inflatable balloon are fabricated from a plastic material that is highly transmissive at the wavelength of the radiant energy being employed.

An elongated, flexible, radiant energy-emitting fiber, having a proximal end and a distal end, is coaxially disposed in the second lumen of the balloon catheter and it extends from the proximal end thereof into its distal end portion. The radiant energy fiber is terminated in a radiant energy diffusing element whose length dimension is less than the predetermined length dimension of the balloon. Furthermore, the radiant energy transmissive fiber is longitudinally displaceable within the second lumen of the angioplasty catheter. A displacement control means is coupled to the proximal end of the balloon catheter and to the fiber for controllably, longitudinally displacing the radiant energy diffusing and emitting element along the predetermined length dimension of the balloon such that the radiant energy, typically UV light in the 240 to 280 nm wavelength range, or perhaps gamma radiation, transmitted through the distal end portion of the tubular catheter body and through the balloon material can be made to bathe the site of the compressed lesion in a series of controlled steps as the balloon is periodically inflated and deflated so as to provide adequate blood supply to tissues downstream of the site being treated. By so moving the radiant energy diffusing member within the confines of the balloon, the irradiated tissue is not subjected to excessive temperature rises.

In accordance with a preferred embodiment of the invention, the controlled longitudinal displacement of the radiant energy diffusing element along the length dimension of the balloon is achieved using a microprocessor controlled stepping motor connected in driving relationship with a lead screw which, when rotated, is effective to translate the optical fiber within the second lumen of the balloon catheter.

DESCRIPTION OF THE DRAWINGS

Further features and objects of the invention will become apparent to those skilled in the art from the following detailed description of a preferred embodiment, especially when considered in conjunction with the accompanying drawings in which like numerals in the several views refer to corresponding parts.

FIG. 1 is a partially cross-sectioned view of the surgical instrument in accordance with the present invention;

FIG. 2 is a cross-sectional view taken along the line 2—2 in FIG. 1; and

FIG. 3 is a side-elevation of a device for controlling the displacement of a radiant energy diffusing element located within the distal end portion of the catheter.

DESCRIPTION OF THE PREFERRED EMBODIMENT

Referring first to FIG. 1, there is identified generally by numeral 10 an instrument especially designed for delivering radiant energy to a site within the vascular system following a balloon angioplasty procedure on a patient. It is seen to comprise an elongated, flexible tubular catheter body 12 having an outer diameter of about 0.040 in. and a wall thickness of approximately 0.005 in. The catheter body is preferably extruded from polyethylene plastic and, as is illustrated in the cross-sectional view of FIG. 2, has at least first and second lumens 14 and 16, respectively.

Appropriately bonded to the exterior surface of the tubular body 12 at the distal end portion thereof is an inflatable expander member or balloon 18, which is circumferentially bonded at its ends 20 and 22 to the tube 12 at spaced apart locations. In accordance with the present invention, the expander member 18 is also preferably formed from polyethylene, a plastic exhibiting high radiant energy transmissivity in the UV light portion of the spectrum. The expander member 18 may typically be anywhere from 20 to 30 mm in length and it spans one or more ports 24 formed through the wall of the catheter body 12 and communicating with the first lumen 14 (FIG. 2), i.e., the inflation lumen. It is also found expedient to locate radiopaque marker bands 26 and 28 on opposite ends of the expander member to facilitate the positioning of the expander member relative to a lesion to be treated under fluoroscopy.

Disposed at the proximal end of the catheter body 12 is a molded plastic hub member 30 which is generally tubular and which has a Touchy-Borst type compression fitting 32 disposed near its proximal end. The hub 30 also includes first and second ports 34 and 36 having Luer fitting for connection to liquid supply tubes (not shown). The port 34 is in fluid communication with the inflation lumen 14 and when a fluid, such as normal saline, is injected under pressure into that port, it flows through the lumen 14 and the ports 24 in the catheter to effect inflation of the expander member 18. The port 36 is in fluid communication with the lumen 16 which extends all the way to the distal end 38 of the balloon catheter. By pumping saline with a roller pump at a low rate of about 2–4 cubic cms per minute into the port 36, the flow prevents blood from entering the distal end 38 of the catheter.

Extending through the compression fitting 32, the tubular hub 30 and through the second lumen 16 of the instrument 10 is an elongated, flexible, radiant energy-transmissive fiber assembly 40. Where the radiation source to be employed is a source of UV light, the radiant energy transmissive fiber may comprise a core member 42 including a quartz fiber 44 covered by a Teflon jacket 46. The wall thickness of the jacket may be approximately 0.003 in. The quartz fiber has a distal end 48 and the jacket 46 extends in the distal direction beyond the end 48 of the fiber for a distance of about 6 mm and forms a radiant energy diffusing and emitting element 50. A radiopaque plug 52 is fitted into the distal end of the element 50.

Starting a predetermined distance proximal of the distal plug 52 and extending proximally through the compression fitting 32 of the hub 30 is an outer tubular reinforcing member 54, which preferably comprises a stainless steel tube whose O.D. is about 0.014 in. The stainless steel reinforcing member 54 tightly surrounds the jacket 46 of the quartz fiber 44 and because of its relative rigidity compared to that of the quartz fiber 44, it permits the radiant energy transmissive fiber assembly 40 to be pushed longitudinally through the lumen 16 of the catheter body 12 when a force is applied at the proximal end of the radiant energy transmissive fiber assembly. The length of the core 42 that extends beyond the distal terminus of the reinforcing member 54 may be approximately 13 in. and, as such, the assembly 40 exhibits sufficient "pushability" and "torqueability" to permit the unreinforced portion to traverse the lumen 16 of the tubular body 12. If gamma radiation is to be delivered to the affected area of the blood vessel, a suitable source of gamma radiation, such as cobalt 60 particles may be embedded in the plastic at the distal end of an elongated flexible fiber.

With continued reference to FIG. 1, there is shown attached to the portion of the radiant energy-transmissive fiber assembly 40 extending proximally beyond the compression fitting 32 an adjustable stop member 56. The stop member 56 can be moved longitudinally along the fiber assembly 40 to a desired position and then locked in place by rotating the knurled grip 58, thereby effectively establishing a predetermined travel distance between the stop member 56 and the proximal end of the hub 30. This also defines the extent of displacement of the diffusing element 50 in the distal direction.

The radiant energy-transmissive fiber assembly 40 extends proximally beyond the stop member 56 and passes through a strain relief member 60, terminating in a standard connector 62. Connector 62 is adapted to couple with the output of a radiant energy source (not shown). The radiant energy source is preferably a pulsed or continuous wave laser capable of producing an output beam at an appropriate UV wavelength. It has been found that a wavelength in the range of from 240 nm to 280 nm covers the range exhibiting efficacy in inhibiting smooth muscle tissue growth.

The UV light emanating from the laser source passes through the quartz fiber 44 to its distal end 48. The Teflon diffusing element 50, comprising the jacket extension, is found to uniformly diffuse the UV light exiting the end of the quartz fiber. Because the tubular body 12 and the expander member 18 are fabricated from a highly UV light transmissive material (polyethylene), the UV light emanating from the diffuser 50 causes a radial band of light, approximately the length of the jacket extension, to radiate out through the expander member to impinge upon the intimal tissue. By controlling the displacement of the fiber in the axial direction, the emanating band of UV radiation can be made to traverse the entire length of the expander member continuously or in discrete steps to thereby expose the adjacent vessel wall to the radiant energy. It is possible, of course, to also rotate the radiant energy transmissive fiber assembly 40 within the lumen of the catheter when and if the radiation pattern exiting the diffusing member is not annularly symmetrical.

Referring next to FIG. 3, there is shown an apparatus for controlling the movement of the radiant energy-transmissive fiber assembly 40 within the lumen 16 of the instrument 10. The apparatus comprises a stationary clamping member 70 having a longitudinal slot 72 formed therein for receiving the tubular barrel of the hub 30. A slide plate 74, when retracted, permits the tubular barrel to be inserted in the slot 72 and when again extended, securely clamps the hub member against longitudinal displacement. The stationary clamping member 70 is affixed to the distal end of a guide member 76 which passes through a slot formed in a movable clamping member 78. The movable clamping member is designed to engage the adjustable stop 56 so that when the movable clamping member 78 is displaced in the direction of the double-headed arrow 80 along the guide 76, the elongated, flexible, light transmissive fiber assembly 40 is likewise translated.

To controllingly displace the moveable clamping member 78, there is provided a stepper motor 82 which is mounted on a base 84 and which is connected in driving relationship to a threaded lead screw 86 supported at its free end in a bearing 88 mounted on a rectangular post 90, also secured to the base 84. The lead screw 86 passes through a threaded bore 92 formed through a rectangular nut 94. The nut is constrained against rotation by a suitable means, such as a Nylon slide bearing 96 that is affixed to the nut 94 and which slidingly cooperates with a surface of the base 84. An elongated segment of piano wire 98 is connected between the traveling nut 94 and the moveable clamping member 78. More particularly, the piano wire 98 passes through a bore 100 formed through a block 102 affixed to the post 90. A tubular sheath 104 surrounds the piano wire between the block 102 and a wire guide 106 formed as a part of the guide member 76. The piano wire 98 is then secured to the moveable clamping member 78 as illustrated.

An electronics module 108 is connected to the motor and contains a microprocessor chip and associated memory for storing a program of instructions controlling the operation of the stepper motor 82. The microprocessor is programmed to supply stepping pulses at a predetermined rate to the motor 82 with each pulse producing a rotation of the lead screw through a predetermined arc and a corresponding translational displacement of the nut 92 and, therefore, the axial disposition of the optical fiber assembly 40 within the lumen 16 of the instrument. The microprocessor is programmed in a known manner to cause the stepper motor to drive the lead screw in accordance with a predetermined time profile, such that the diffuser 50 traverses the length dimension of the balloon 18, either continuously or in a series of discrete steps, each with a predetermined dwell time, as the radiant energy source connected to the proximal end connector 62 of the assembly of FIG. 1 transmits the energy down the quartz fiber 44. At the same time, a roller pump coupled to a bag of normal saline (neither shown) can be made to infuse the lumen 16 of the catheter, via the flush port 36, to establish a positive flow in the distal direction, preventing ingress of blood which might otherwise interfere with the transmission of UV light or other radiant energy from the diffuser to the wall of the artery being treated. Also, by controlling the pressure of fluid at the inflation port 34, the balloon can be periodically inflated and deflated during the procedure so that an adequate blood supply is provided distal of the treatment site to nourish the heart muscle. In fact, the energization of the radiation source, the displacement of the optical fiber and the inflation/deflation of the balloon can be appropriately synchronized.

By positioning the adjustable stop member 56 on the stainless steel sleeve 54 surrounding the light fiber assembly, a limit is established, preventing the distal end of the light fiber from exiting the distal end of the catheter. By providing a radiopaque plug 52 in the distal end of the jacket extension, the position of the diffuser 50 relative to the radiopaque markers 26 and 28 assists the cardiologist in following the progress of the radiant energy treatment of the blood vessel wall.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Apparatus for treating the wall of a lumen of a tubular vessel to modify the tissue for therapeutic benefit comprising, in combination:

(a) a catheter having an elongated, flexible tubular catheter body with a proximal end, a distal end portion, first and second lumens extending through the tubular body and an inflatable balloon of a predetermined length dimension disposed proximate the distal end portion of the tubular catheter body and in fluid communication with the first lumen, both the distal end portion of the tubular catheter body and the inflatable balloon being made from a radiant energy-transmissive material;

(b) an elongated, flexible, radiant energy-emitting fiber having a proximal end and a distal end, the radiant energy-emitting fiber being coaxially disposed in the second lumen and extending from the proximal end of the tubular catheter body to the distal end portion, the radiant energy-emitting fiber being displaceable longitudinally within the second lumen;

(c) the radiant energy-emitting fiber including an elongated, flexible optical waveguide core having an elastomeric jacket thereon, the jacket having a segment extending beyond a distal end of the core, the segment comprising the radiant energy diffusing element;

(d) a reinforcing tubular member coaxially disposed about the jacket and extending from the proximal end of the radiant energy-emitting fiber toward, but short of, the distal end of the radiant energy-transmissive fiber by a predetermined length dimension greater than the predetermined length dimension of the diffusing element;

(e) means for supplying the radiant energy-emitting fiber from a source of radiant energy of a selected wavelength and energy insufficient to effect tissue necrosis; and (f) means coupled to the proximal end of the catheter body and to the radiant energy-emitting fiber for controllably longitudinally displacing the distal end of the radiant energy-emitting fiber along the predetermined length dimension of the balloon to expose a wall surface of the lumen of the tubular vessel to radiant energy of a predetermined wavelength.

2. The apparatus as in claim 1 wherein said source of radiant energy produces UV radiation whose wavelength is in the range of from 240 nm to 280 nm.

3. The apparatus as in claim 1 wherein the inflatable balloon is an oriented polyethylene film.

4. The apparatus as in claim 3 wherein the distal end portion of the tubular catheter body is made of polyethylene.

5. The apparatus as in claim 1 wherein the means coupled to the proximal end of the tubular catheter body and to the radiant energy-emitting fiber for controllably longitudinally displacing the radiant energy diffusing element comprises a stepping motor.

6. The apparatus as in claim 5 and further including a microprocessor-based controller coupled in controlling relation to said stepping motor for furnishing drive pulses thereto in accordance with a predetermined program.

7. The apparatus as in claim 5 and further including a slide block connected to the radiant-energy-emitting fiber and a stationary block connected to the proximal end of the tubular catheter body, the stepping motor being operatively coupled to the slide block.

8. The apparatus as in claim 7 wherein the stepping motor is operatively coupled to the slide block by a lead screw, the lead screw including a traveling nut, and means coupling the traveling nut to the slide block.

9. The apparatus as in claim 1 and further including a radiopaque plug disposed in a distal end of the extending segment of the jacket.

10. The apparatus as in claim 9 and further including a tubular hub member affixed to the proximal end of the tubular catheter body, the tubular hub member having a first port in fluid communication with the first lumen and a second port in fluid communication with the second lumen.

11. The apparatus as in claim 10 and further including a third port on the hub member leading to the second lumen, the third port including a compression fitting for clamping engagement with the reinforcing tubular member.

12. The apparatus as in claim 11 and further including a stop member coaxially surrounding the reinforcing tubular member at a location proximal to the compression fitting, the stop member establishing a maximum displacement of the radiant energy-emitting fiber in a distal direction within the second lumen.

13. A method for treating the wall of a lumen of a tubular vessel to modify the tissue for therapeutic benefit comprising the steps of:

(a) introducing into the tubular vessel a catheter having an elongated flexible tubular body with an inflatable balloon attached thereto at a distal end thereof and first and second lumens extending the length of the flexible tubular body, one of the first and second lumens being in fluid communication with the inflatable balloon, the inflatable balloon and the portion of the tubular body to which the balloon is attached being made of a radiant energy transmissive material, the other of the first and second lumens containing an elongated, flexible radiant energy transmissive fiber with a radiant energy emitting surface at a distal end thereof, the radiant-energy transmissive fiber being surrounded by an elastomeric jacket with a segment extending beyond a distal end of the radiant energy transmissive fiber, the segment being a radiant energy diffusing element of a predetermined length dimension and a reinforcing tubular member coaxially disposed about the jacket and extending from a proximal end of the radiant energy-emitting fiber toward, but short of, the distal end of the radiant-energy transmissive fiber by a predetermined length dimension greater than the predetermined length dimension of the diffusing element;

(b) connecting a proximal end of the radiant energy transmissive fiber to a source of radiant energy of a predetermined wavelength;

(c) inflating the balloon with a radiant energy transmissive fluid to displace blood away from the tissue to be modified; and (d) longitudinally displacing the optical fiber within the second lumen such that radiant energy emitted from said surface is made to scan the wall of the lumen of the tubular vessel being treated in accordance with a predetermined exposure profile.

14. The method as in claim 13 and further including the step of periodically deflating the balloon at predetermined intervals to permit blood flow distal of the inflatable balloon.

15. The method as in either of claims 13 or 14 wherein the source of radiant energy provides UV light whose wavelength is in the range of from 240 nm to 280 nm.

* * * * *